United States Patent [19]

Suzuki et al.

[11] Patent Number: 4,892,528
[45] Date of Patent: Jan. 9, 1990

[54] DISPOSABLE DIAPER

[75] Inventors: Migaku Suzuki, Kawanoe; Mitsuzo Ochi, Ehime; Takeshi Kudo, Kawanoe, all of Japan

[73] Assignee: Uni-Charm Corporation, Ehime, Japan

[21] Appl. No.: 269,298

[22] Filed: Nov. 10, 1988

Related U.S. Application Data

[63] Continuation of Ser. No. 69,181, Jul. 1, 1987, abandoned.

[30] Foreign Application Priority Data

Jul. 4, 1986 [JP] Japan .................................. 61-158609
Aug. 20, 1986 [JP] Japan .................................. 61-194500

[51] Int. Cl.⁴ ............................................ A61F 13/16
[52] U.S. Cl. .................................................. 604/385.2
[58] Field of Search ............ 604/385.2, 385 R, 385 A, 604/357, 367, 370, 372, 373, 378, 366, 358

[56] References Cited

U.S. PATENT DOCUMENTS

| | | | |
|---|---|---|---|
| 2,273,542 | 2/1942 | Tasker | 604/385.2 |
| 4,692,163 | 9/1987 | Widlund et al. | 604/385.2 |
| 4,695,278 | 9/1987 | Lawson | 604/385.2 |
| 4,699,620 | 10/1987 | Bernardin | 604/385.2 |

Primary Examiner—Larry Jones
Attorney, Agent, or Firm—Fred Philpitt

[57] ABSTRACT

Here is disclosed a disposable diaper comprising an absorbent core of a desired thickness, a water-permeable topsheet covering at least an upper surface of said core, a water-proof or a water-impervious backsheet covering at least a bottom surface of said core, water-impervious side flaps extending outwardly of opposite sides of said core, first elastic bands adapted to form elastic gathers longitudinally of the respective flaps and leakage protecting baffles formed along opposite side edges of said core and contained second elastic bands to provide elastic gathers longitudinally thereof.

9 Claims, 3 Drawing Sheets

DISPOSABLE DIAPER

This is a continuation of application Ser. No. 69,181, filed July 2, 1987, now abandoned, and the benefits of 35 USC 120 are claimed relative to it.

BACKGROUND OF THE INVENTION

TECHNICAL FIELD

The present invention relates to a disposable diaper and particularly to such diaper characterized by a structure for prevention of excretion leakage.

PRIOR ART

French Patent Publication No. 2,388,515 discloses a disposable diaper having no side flaps closely surrounding thighs of the wearer, wherein opposite sides of an impervious backsheet extending on the underside of an absorbent core are folded upward so as to cover opposite sides of said core and opposite side edges of a pervious topsheet are provided longitudinally of them as well as flatly thereon with elastic bands to form gathers. The invention on which this patent application is based essentially resides in that the respective zones of said topsheet and said backsheet in which said elastic bands adhere to these both sheets are set free from said core and thereby the elasticity of said elastic bands is relieved a restricting effect exerted by the rigidity of said core.

U.S. Pat. No. 4,579,556 discloses an absorbent article such as a disposable diaper having side flaps closely surrounding thighs of the wearer, wherein said flaps are formed by folding opposite sides of a impervious backsheet disposed on the underside of an absorbent core so as to extend outwardly of opposite side edges of said core and then fastening said folded side edges to a pervious topsheet disposed on the upper side of said core and wherein said flaps are provided with elastic bands being elastic longitudinally of said flaps so that said flaps are raised by the elasticity of said bands along zones adjacent said core. This invention generally resides in that body fluids are prevented from leaking out along the opposite side edges of said core and a fitness of the article to the body of the wearer is improved.

PROBLEMS TO BE SOLVED BY THE INVENTION

In the disposable diaper, fluffy pulp has generally been used as main material for the absorbent core and, to improve its absorbability, various measures have been employed such as embossing and mixing of highly absorptive polymer particles. However, absorbing rates of said topsheet and said core are not adequately high to absorb a quantity of urine at once as soon as said quantity of urine excreted onto the upper surfaces of said topsheet and said core, as that the urine, at least partially, flows on the upper surface of said sheet laterally and often leaks out along the opposite side edges of the diaper. It is obvious that such a leakage will readily occur when the quantity excreted at once is relatively plenty.

With the invention disclosed in French Patent Publication No. 2,388,515, it is merely provided that the elastic bands are brought into close but flat contact with thighs of the wearer for prevention of excretion leakage. Accordingly, gaps are apt to be formed between the zones of the diaper into which said bands are incorporated and the wearer's skin when the wearing condition of the diaper deviates from the correct condition even through such deviation is slight or when the wearer takes a certain a posture as the wearer moves. In consequence, there is a possibility that not only said quantity of urine laterally flowing but also even liquid excrement (loose passage) leaks out through said gaps.

In case of the invention disclosed in U.S. Pat. No. 4,579,556, the opposite side edges of the absorbent core is covered with a part of the impervious backsheet and thereby a certain degree of leakage protecting effect is achieved. However, as has previously been pointed out, there still remains a possibility that, when a quantity of urine is excreted at once onto the top surface of the diaper immediately under which the absorbent core is disposed, a partial quantity of urine laterally flows on the topsheet and leaks out along the opposite side edges of the diaper before said quantity of urine is effectively absorbed by said core and blocked by said impervious side edges. Even through the side flaps are raised under the elasticity of the elastic bands on the opposite side edges of said core, these side flaps are inevitably collapsed outwardly of said side edges of said core once the diaper has been worn by the user, since said side flaps are subjected to the body pressure, so that it is difficult for said leakage protecting effect to be expected.

OBJECT OF THE INVENTION

An essential object of the present invention is to provide a disposable diaper permitting the problems left unsolved by said prior art to be effectively solved by providing the side flaps with elastic bands, covering opposite side edges of the absorbent core with a part of the backsheet while bestowing said opposite side edges with a baffle function including a spatial elastic structure, and, in the most preferred embodiment, constructing an upper portion of said core with an isolating layer of a low fibrous density and having a large vacant space while utilizing the topsheet having a plurality of apartures.

SUMMARY OF THE INVENTION

In view of the object as set forth above, the present invention provides a disposable diaper comprising an absorbent core of a desired thickness, a water-permeable topsheet covering at least an upper surface of said core, a waterproof or a water-impervious backsheet covering at least a bottom surface of said core, water-impervious side flaps extending outwardly of opposite sides of said core, first elastic bands adapted to form elastic gathers longitudinally of the respective flaps and leakage protecting baffles formed along opposite side edges of said core to provide elastic gathers longitudinally thereof, wherein said leakage protecting baffles are raised from upper edges of the opposite sides of said core under elasticity of associated second elastic bands being longitudinally elastic.

According to the present invention, even when liquid excretion is absorbed by the absorbent core and then reaches the opposite side edges of said core, there occurs no leakage along the opposite sides of the core, since these opposite sides of the core are covered with the water-proof sheet. Furthermore, even in a situation that liquid excretion overflows the top surface of the core and flows toward the opposite side edges thereof before completely absorbed by the core, a leakage occurring along the opposite side edges of the diaper is reduced to the minimum, since there are provided at the opposite sides of the core the water-impervious leakage protecting baffles extending along the upper edges of the respective sides, which baffles respectively form the gathers and thereby to prevent a leakage from occurring along these zones. Should liquid excretion flows over the leakage protecting baffles to the respective side flaps located outside thereof, a quantity of such flow is far less than the case in which there is no leakage protecting baffles and can be adequately prevented from further flowing out by the side flaps closely surrounding the thighs of the wearer under the elasticity of the elastic bands incorporated into the respective side flaps.

Although the leakage protecting baffles are apt to be outwardly tilted or collapsed under a body pressure of the wearer, the elastic bands incorporated into the respective baffles tend to maintain these baffles upstanding so as to minimize a possibility that the baffles might be disengaged from the wearer's skin to form gaps therebetween.

The second elastic bands forming parts of the leakage protecting baffles are maintained stretched to some degree so long as the diaper is put on the wearer's body, making the wearer free from any uncomfortable feeling and effectively preventing folds causing leakage from being formed in the topsheet and the core.

PREFERRED EMBODIMENTS

The invention will be described by way of example in reference with the accompanying drawing.

Figure 1:
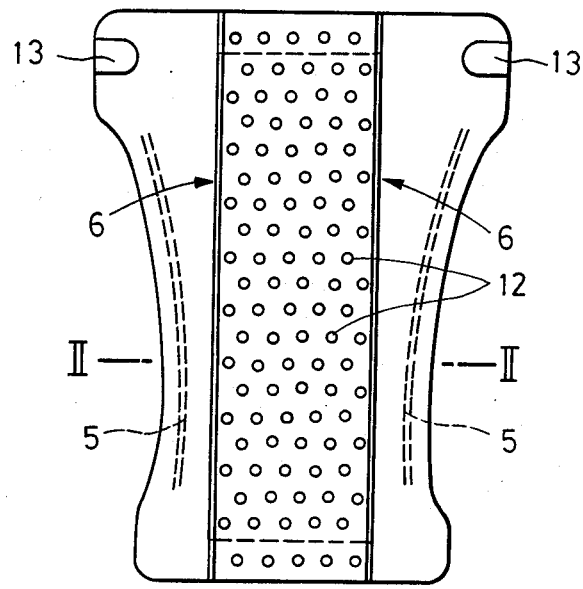
FIG. 1 is a plan view showing an embodiment of the diaper constructed according to the present invention as being unfolded.
Figure 2:
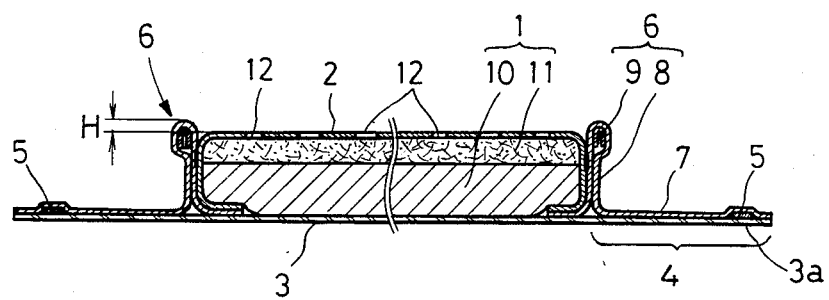
FIG. 2 is a section taken along a line II—II in FIG. 1.

As shown in FIGS. 1 and 2, the diaper includes an absorbent core 1 of a desired thickness, a water-permeable topsheet 2, a water-proof or water-impervious backsheet 3, water-impervious side flaps 4, elastic bands 5 and leakage protecting baffles 6.

The topsheet 2 covers the core 1 over its top surface and around its peripheral edge. The backsheet 3 covers the bottom surface of the core 1 and outwardly extends beyond the peripheral edge of the core 1. The side flaps 4 comprise opposite extensions 3a of the backsheet 3 and water proof or water-impervious sheets 7 fastened to respective top surfaces thereof.

The elastic bands 5 are made of such material as natural or synthetic rubber or plastics, and adhesively interposed between the associated extensions 3a and the sheets 7 together forming the respective side flaps 4. To assure a good fitness of the diaper to the wearer's body, a distance between the pair of elastic bands 5 is diverged from a front zone to a rear zone of the diaper as seen in the unfolded condition of the latter.

Figure 3:
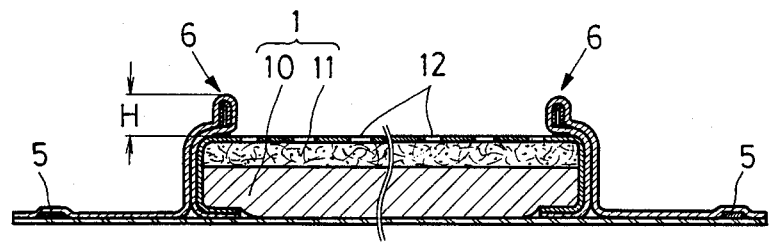
FIG. 3 and 4 are sections taken along a line II—II in FIG. 1, but showing other embodiments, respectively.

The leakage protecting baffles 6 comprises a part of the respective sheet 7 upwardly projecting in an inverted U-or Ω-shape, containing an elastic band 9 being longitudinally elastic. This elastic band 9 is adhesively fixed to the inner side of the projection 8 thus formed and the leakage protecting baffle 6 as a whole projects above the upper surface of the core along the opposite sides thereof. It is preferred that the inner side of said projection 8 is intermittently fastened to the zone of the topsheet 2 located along the one of the opposite sides of the core 1 and this fastening is effected at least adjacent the upper edge of said zone. A height H of the leakage protecting baffle 6 as measured from the upper surface of the topsheet 2 corresponding to the upper edge of the opposite sides of the core 1 is 3 to 20 mm, preferably 5 to 15 mm. The leakage protecting baffles 6 shown in FIG. 3 are inwardly folded adjacent the upper ends thereof over the opposite sides of the core 1. In this case, the folded portions of the respective baffles 6 are preferably fastened to the upper surface of the topsheet 2 at least along the corresponding upper edges of the opposite sides of the core 1. Each of the elastic bands 9 may be of the material similar to that for said band 5. Ribbon or tape of such material is transversely curved in an inverted U-shape and disposed within an upper half of the projection 8. Although it is not important that the elastic bands 9 are made of any particular material in any particular shape and whether each of them is disposed within the upper half of the projection 8 or not and whether each of them fully occupies the interior of said projection 8 or not, the elastic bands 9 are preferably disposed in the respective projections 8 adjacent the top portion thereof, so far as the elastic bands 9 present the desired elasticity. In other words, the leakage protecting baffles 6 are maintained upstanding on the upper edges of the opposite sides of the core 1 irrespectively of their material, shape and location, under a tensile force due to the contractibility of the elastic bands 9 tending to raise the respective baffles 6 into a bow-shape. It should be noted here that each of the leakage protecting baffles 6 has its longitudinally opposite ends preferably collapsed outwardly and fixed in such condition, because a portion of the elastic band 9 defined between these opposite ends is given a tendency to be tilted outwardly and an undesired tendency of the band 9 to be tilted inwardly when the diaper is put on the body of the wearer is avoided by this arrangement.

The core 1 comprises an absorbent retaining layer 10 consisting of fluffy pulp, fibrous web or nonwoven fabric containing highly absorptive polymers (not shown) mixed therein and an isolating layer 11 in the form of fibrous web having a relatively low density so as to define a large vacant space therein and exhibiting a high compressive elasticity recovery rate under wet condition. The isolating layer 11 is disposed between the topsheet 2 and said absorbent retainer layer 10, isolating the both from each other and allowing liquid excretion to pass rapidly therethrough. The isolating layer 11 functions not only to reduce a possibility that a quantity of liquid excretion which has been absorbed by the absorbent retaining layer 10 might flow again to the top surface of said absorbent retaining layer 10 and soak through the topsheet 2 but also to give the core 1 a cushion-like nature so as to make the wearer free from any rigid feeling. To perform such functions adequately, the isolating layer 11 preferably comprises fibers each being of 35 to 100 mm length and welded together at intersecting points to maintain a shape of web. Individual fibers are preferably hydrophobic fibers of which at least 50% by weight are water-absorptive (so-called sweat-absorptive), particularly sweat-absorptive polyester fibers. To facilitate the fiber welding, the fibers preferably contain at most 30% by weight of low melting point (110° to 200° C.) polyester fibers, polyethylene fiber, polypropylene fibers, or conjugate fibers (side-by-side, core - sheath type) of polyethylene/polypropylene low melting point polyester/ordinary polyester. The isolating layer 11 has a thickness of 2 to 10 mm as measured after placed under a load of 3 g/cm² for 1 minute, a weight per unit area of 20 to 80 g/m², a compressive elasticity recovery rate under wet condition higher than 30%, preferably higher than 50% and a fineness of 3 to 13d.

The topsheet 2 is maintained by fibers entangled together in a configuration of nonwoven fabric and provided with a plurality of regularly arranged apertures 12 all over the surface therethrough. These apertures 12 are formed by distribution of the fibers. Each of these apertures 12 preferably has a distinct outline without any fibers extending across this aperture. Such topsheet 2 is obtained, for example, by a method in which fibrous web is introduced onto a support member provided thereon a plurality of projections and a high velocity water stream is jetted from above to said fibrous web so as to effect desired fiber entanglement as well as to move the fibers aside on the respective projections. For the apertures 12 each being circular and having an area of 7 to 50 mm², a diameter of 2 to 10 mm, an array pitch of 6 to 20 mm and a total aperture ratio with respect to all the surface area of 15 to 70% are preferable. The topsheet 2 is so constructed that the body fluids such as urine and sweat freely pass therethrough without soaking the surface of the non-apertured zone and previously treated with water repellent of well known art. It is preferred that 70 or higher % by weight of rayon fibers having a fineness of 0.5 to 3d are contained in the topsheet 2. However, 70 or higher % by weight of said water-absorptive fibers or ordinary hydrophobic fibers may be contained and one of the most preferable fibers is polyester fiber having a fineness of 1 to 3d. The topsheet 2 generally has a weight per unit area is 15 to 45 g/m².

The backsheet 3 comprises air-permeable liquid-resistant plastic film or laminate of the latter and fibrous nonwoven fabric.

The water-impervious sheet 7 forming a part of each side flap 4 preferably comprises an air-permeable sheet of nonwoven fabric, particularly, spunbond nonwoven fabric of polypropylene which has been water-repellent treated.

The diaper thus constructed is, just as in the case of the well known disposable diaper, assembled and put on the wearer's body by fastening free ends of tape fasteners 13 mounted on the opposite sides of the rear zone at a level of the waist line to the opposite sides of the backsheet 3 in the front zone.

Figure 4:
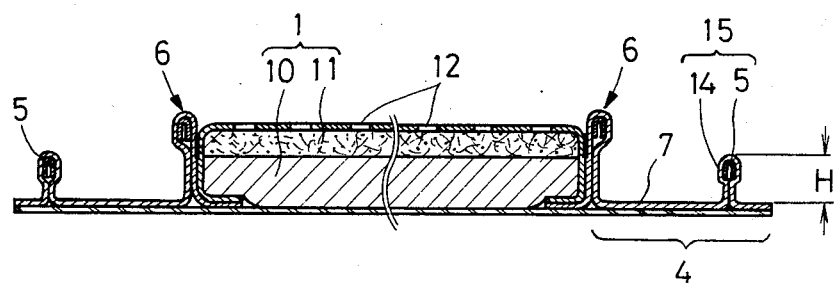

FIG. 4 shows an embodiment of the present invention in which the sheet 7 forming a part of each side flap 4 partially projects in an inverted U- or ω-shape and a projection 14 thus formed contains thereinside an elastic band 5 transversely curved in an inverted U-shape so as to form a leakage protecting baffle 15. This baffle 15 is also, as in the case of the previously mentioned leakage protecting baffle 6, has its height H and its longitudinally opposite ends preferably outwards collapsed and fixed.

Figure 5:
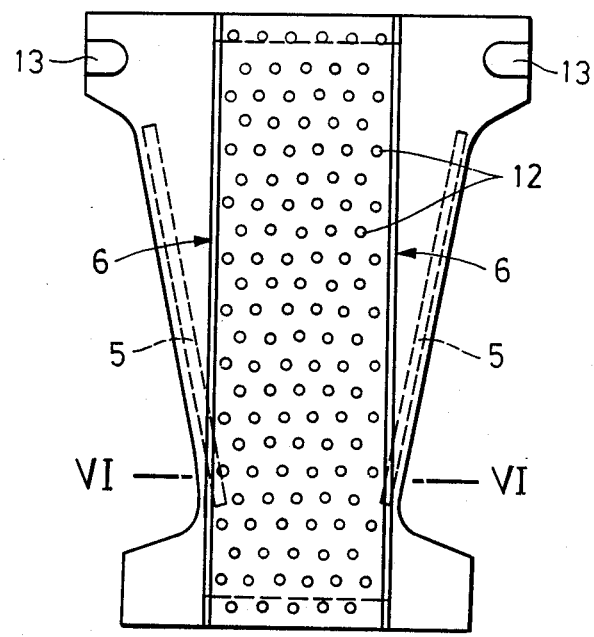
FIG. 5 is a plan view showing further embodiment of the diaper according to the present invention as being unfolded.
Figure 6:
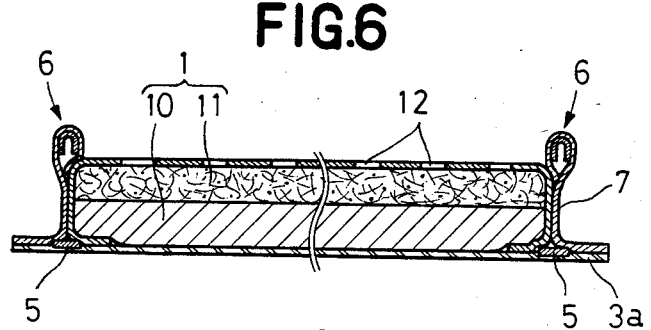
FIG. 6 is a section taken along a line VI—VI in FIG. 5.

FIGS. 5 and 6 show another embodiment of the present invention in which each of the side flaps 4 is tapered from the rear zone to the front zone and each of the elastic bands 5 is disposed between an extension 3a of the backsheet forming the side flap 4 and the sheet 7. A distance between the pair of the elastic bands 5 is correspondingly reduced from the rear zone to the front zone of the diaper and the front portions of the bands 5 are located on the bottom edges of the opposite sides of the core 1 and intersect them. However, these front portions may be adjacent, instead of intersecting them.

Figure 7:
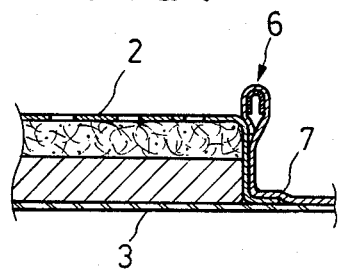
FIG. 7 is a partial section of still another embodiment of the diaper according to the present invention.

It should be understood that the opposite side edges of the topsheet 2 may, as seen in FIG. 7, extend outwardly. Furthermore, the leakage protecting baffles 6 and 15 may be disposed at lease in the crotch area of the diaper.

What is claimed is:

1. A disposable diaper comprising in combination
   (a) a thick absorbent core (1) having a top surface, a bottom surface and two side surfaces,
   (b) a top sheet (2) extending over both the top surface and the two side surfaces of said absorbent core (1), the portion of said top sheet (2) that extends over the top surface of said adsorbent core (1) being water-permeable,
   (c) a water-impermeable backsheet (3) extending over the major portion of the bottom surface of said absorbent core (1) and having two lateral portions that extend laterally outwardly from the sides of said absorbent core (1),
   (d) two sheets (7) resistant to the passage of water disposed adjacent to and at least partially outwardly from the two side surfaces of said absorbent core,
      (i) the outer portion of each of said sheets (7) being joined to the portions of said water-impermeable backsheet (3) that extend laterally from the sides of said absorbent core (1) so that together they form side flaps (4),
      (ii) the inner portion of each of said sheets (7) being formed into the general shape of an inverted "U" (8) that has the two ends of the "U" facing toward said backsheet (3) with one section of said inner portion being disposed in a parallel relationship to and in close proximity to the portion of said top sheet (2) that extends along the sides of said absorbent core (1), said inverted "U" portion (8) extending above said backsheet (3) to a point which is above the top surface of said absorbent core (1) so as to form a leakage-protecting baffle (6) that extends above the top surface of said absorbent core (1),
   (e) a length of elastic material (9) disposed within the inverted "U" inner portion (8) of each of said sheets (7), and
   (f) an elongated elastic band (5) joined to each side flap (4).

2. A diaper according to claim 1 wherein the side flaps (4) set forth in (d)(i) are deformed to form a second leakage protecting baffle (15).

3. A disposable diaper comprising:
   (a) a water-permeable topsheet (2),
   (b) a water-impermeable backsheet (3),
   (c) an absorbent core (1) interposed between said topsheet (2) and backsheet (3),
   (d) a side-flap (4) extending outwardly from an outer edge of said absorbent core (1),
   (e) a first elasticized leakage protecting baffle (6) that extends above the top surface of said absorbent core (1) from said side-flap (4), (f) a second elasticized leakage protecting baffle (14) disposed outwardly of said first baffle (6) and also projecting from said side-flap (4), and (g) a sheet (7) resistant to the passage of water including an inner portion having elastic means (9), an outer portion having elastic means (5), wherein said first and second elasticized leakage protecting baffles (6, 14) respectively comprise the inner and outer portions of said sheet (7).

4. The diaper of claim 3 wherein the first elasticized leakage protecting baffle (6) includes an inner surface at least partially secured to said topsheet (2) adjacent to said core edge (1).

5. The diaper of claim 3 wherein said first elasticized protecting baffle (6) is folded inwardly and secured at its longitudinal ends to the diaper.

6. The diaper of claim 3 wherein said sheet (7) comprises an air-permeable nonwoven fabric.

7. The diaper of claim 6 wherein said sheet (7) comprises a spunbonded nonwoven fabric that is treated to be water-repellent.

8. A disposable diaper comprising:

(a) a water-permeable topsheet (2), (b) a water-impermeable backsheet (3), (c) an absorbent core (1) interposed between said topsheet (2) and backsheet (3), (d) a side-flap (4) including at least a lateral portion of said backsheet (3) that extends laterally outwardly from a lateral edge of said absorbent core (1), (e) a sheet (7) resistant to the passage of water, having inner and outer portions, the outer portion being joined to said side-flap (4) and the inner portion having first elastic means (9) for forming an elasticized leakage protecting baffle that projects upwardly from said side-flap (4), and (f) second elastic means (5) secured between the outer portion of said sheet (7) and the lateral portion of said backsheet (3) to form an elastic line therethrough;

whereby a barrier against liquid flow is provided beneath said sheet (7).

9. The diaper of claim 8 wherein said sheet (7) comprises a nonwoven fabric that is treated to be water-repellent.

* * * * *